United States Patent
Ono et al.

(10) Patent No.: US 11,417,144 B2
(45) Date of Patent: Aug. 16, 2022

(54) PROCESSING APPARATUS, FINGERPRINT IMAGE EXTRACTION PROCESSING APPARATUS, SYSTEM, PROCESSING METHOD, AND COMPUTER READABLE MEDIUM

(71) Applicant: NEC Corporation, Tokyo (JP)

(72) Inventors: Yoshimasa Ono, Tokyo (JP); Shigeru Nakamura, Tokyo (JP); Atsufumi Shibayama, Tokyo (JP); Junichi Abe, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 17/431,784

(22) PCT Filed: Feb. 22, 2019

(86) PCT No.: PCT/JP2019/006847
§ 371 (c)(1),
(2) Date: Aug. 18, 2021

(87) PCT Pub. No.: WO2020/170439
PCT Pub. Date: Aug. 27, 2020

(65) Prior Publication Data
US 2022/0139105 A1 May 5, 2022

(51) Int. Cl.
*G06V 40/12* (2022.01)
*G06V 40/13* (2022.01)
(Continued)

(52) U.S. Cl.
CPC ............ *G06V 40/1341* (2022.01); *G06T 7/13* (2017.01); *G06T 7/50* (2017.01); *G06T 7/73* (2017.01);
(Continued)

(58) Field of Classification Search
CPC .......... G06V 40/1341; G06V 40/1318; G06V 40/1335; G06V 40/1359; G06V 40/1376;
(Continued)

(56) References Cited

U.S. PATENT DOCUMENTS

2012/0063660 A1 3/2012 Imamura et al.
2017/0083742 A1 3/2017 Lamare et al.
(Continued)

FOREIGN PATENT DOCUMENTS

JP H07-73291 A 3/1995
JP 2010-051347 A 3/2010
(Continued)

OTHER PUBLICATIONS

Supriyanti, Retno & Witno, Suwitno & Ramadhani, Yogi & Widodo, Haris & Rosanti, Tutik. (2016). Brightness and Contrast Modification in Ultrasonography Images Using Edge Detection Results. TELKOMNIKA (Telecommunication Computing Electronics and Control). 14. 1090-1098. 10.12928/TELKOMNIKA.v14i3.3440. (Year: 2016).*

(Continued)

*Primary Examiner* — Abhishek Sarma
(74) *Attorney, Agent, or Firm* — Sughrue Mion, PLLC

(57) ABSTRACT

A technique for accurately extracting a fingerprint image for accurate authentication from 3D tomographic luminance data of a finger at a high speed. A processing apparatus (11) according to the present disclosure includes means for, after performing edge detection processing on a tomographic image (101, 102, ... 10 k, ..., 10n) at each depth, calculating the total number of edge pixels in the tomographic image from 3D (three-dimensional) tomographic luminance data, and acquiring depth dependence of the number of edges (111, 112), and means for extracting a tomographic image having a striped pattern from the depth (Continued)

dependence of the number of edges and the 3D tomographic luminance data.

11 Claims, 13 Drawing Sheets

(51) Int. Cl.
    *G06T 7/50* (2017.01)
    *G06T 7/73* (2017.01)
    *G06T 7/13* (2017.01)
(52) U.S. Cl.
    CPC ...... *G06V 40/1318* (2022.01); *G06V 40/1335* (2022.01); *G06V 40/1359* (2022.01); *G06V 40/1376* (2022.01); *G06V 40/1388* (2022.01); *G06V 40/1394* (2022.01); *G06T 2207/10101* (2013.01)
(58) Field of Classification Search
    CPC .. G06V 40/1388; G06V 40/1394; G06T 7/13; G06T 7/50; G06T 7/73; G06T 2207/10101
    See application file for complete search history.

(56) References Cited

U.S. PATENT DOCUMENTS

| | | |
|---|---|---|
| 2018/0173936 A1 | 6/2018 | Mizoguchi |
| 2019/0012805 A1* | 1/2019 | Bertram ................. A61B 6/032 |

FOREIGN PATENT DOCUMENTS

| | | |
|---|---|---|
| JP | 2010-279440 A | 12/2010 |
| JP | 2013-022338 A | 2/2013 |
| WO | 2016/204176 A1 | 12/2016 |

OTHER PUBLICATIONS

International Search Report for PCT Application No. PCT/JP2019/006847, dated Apr. 23, 2019.
Bossen, R. Lehmann et al., "Internal fingerprint identification with optical coherence tomography", IEEE Photonics Technology Letters, vol. 22, No. 7, pp. 507-509, Apr. 1, 2010.
M. Liu et al., "Biometric mapping of fingertip eccrine glands with optical coherence tomography", IEEE Photonics Technology Letters, vol. 22, No. 22, pp. 1677-1679, Nov. 15, 2010.

* cited by examiner

PROCESSING APPARATUS, FINGERPRINT IMAGE EXTRACTION PROCESSING APPARATUS, SYSTEM, PROCESSING METHOD, AND COMPUTER READABLE MEDIUM

This application is a National Stage Entry of PCT/JP2019/006847 filed on Feb. 22, 2019, the contents of all of which are incorporated herein by reference, in their entirety.

TECHNICAL FIELD

The present disclosure relates to a processing apparatus, a fingerprint image extraction processing apparatus, a system, a processing method, and a computer readable medium for improving accuracy of authentication.

BACKGROUND ART

As a technique for taking a tomographic image of a part of an object to be measured near the surface thereof, there is an Optical Coherence Tomography (OCT) technology. In this OCT technology, a tomographic image of a part of an object to be measured near the surface thereof is taken by using interference between scattered light that is emitted from the inside of the object to be measured when a light beam is applied to the object to be measured (hereinafter referred to as "back-scattered light") and reference light. In recent years, this OCT technology has been increasingly applied to medical diagnoses and inspections of industrial products.

The OCT technology has been practically used for tomographic imaging apparatuses for fundi of eyes in ophthalmic diagnoses, and has been studied in order to apply it as a noninvasive tomographic imaging apparatus for various parts of living bodies. In the present disclosure, attention is focused on a technique for dermal fingerprint reading using the OCT technology.

As a technique for using a fingerprint as biometric information, a biometric authentication technique using 2D (two-dimensional) image data of an epidermal fingerprint has been widely used. On the other hand, tomographic data of a finger acquired by using the OCT technology is luminance data at a 3D (three-dimensional) place. That is, in order to use data acquired by the OCT technology for the conventional fingerprint authentication based on 2D images, it is necessary to extract a 2D image containing features of the fingerprint from 3D tomographic data.

As a related art of the present invention, in Non-patent Literatures 1 and 2, a dermal fingerprint image is acquired by averaging tomographic luminance images over a predetermined range in the depth direction in tomographic data of a finger. However, a range of depths in which a dermal fingerprint is shown is hypothetically determined, and a fixed value is used for the predetermined range.

Further, in Patent Literature 1, a luminance change in the depth direction is obtained for each pixel in a tomographic image. Then, a depth at which the luminance is the second highest is selected as a depth at which a dermal fingerprint is shown, and an image at this depth value having the luminance value is used as a dermal fingerprint image.

CITATION LIST

Patent Literature

Patent Literature 1: United States Patent Application Publication No. 2017/0083742

Non Patent Literature

Non-patent Literature 1: A. Bossen, R. Lehmann and C. Meier, "Internal fingerprint identification with optical coherence tomography", IEEE Photonics Technology Letters, vol. 22, no. 7, 2010

Non-patent Literature 2: M. Liu and T. Buma, "Biometric mapping of fingertip eccrine glands with optical coherence tomography", IEEE Photonics Technology Letters, vol. 22, no. 22, 2010

SUMMARY OF INVENTION

Technical Problem

In the above-mentioned Non-patent Literatures 1 and 2, since the averaging process is performed for tomographic luminance images over the fixed range of depths, differences of thicknesses of epidermises among individuals are not taken into consideration. For example, when an epidermis has been worn or has become thick due to the occupation, the averaging may be performed over a range of depths that is deviated from the range of depths in which a dermal fingerprint is clearly shown, therefore making it difficult to obtain a clear dermal fingerprint image.

In the aforementioned Patent Literature 1, since the depth at which a dermal fingerprint is clearly shown is determined for each pixel in a tomographic image, the measurement is likely to be affected by noises caused by the measuring apparatus using the OCT technology itself, so that there is a high possibility that the depth is incorrectly determined. Further, since the process for determining a depth is performed for each pixel in a tomographic image, it takes time to extract a dermal fingerprint image.

An object of the present disclosure is to provide a processing apparatus, a fingerprint image extraction processing apparatus, a system, a processing method, and a computer readable medium for solving the above-described problems.

Solution to Problem

A processing apparatus according to the present disclosure includes:

means for, after performing edge detection processing on a tomographic image at each depth, calculating the total number of edge pixels in the tomographic image from 3D (three-dimensional) tomographic luminance data, and acquiring depth dependence of the number of edges; and means for extracting a tomographic image having a striped pattern from the depth dependence of the number of edges and the 3D tomographic luminance data.

A fingerprint image extraction processing apparatus according to the present disclosure includes:

dividing means for acquiring 3D partial tomographic luminance data by dividing the 3D tomographic luminance data at a plane perpendicular to a direction toward inside of a target object;

means for, after performing edge detection processing on a tomographic image at each depth, calculating the total number of edge pixels in the tomographic image from the 3D partial tomographic luminance data, acquiring depth dependence of the number of edges, extracting a partial image having a striped pattern from the depth dependence of the number of edges and the 3D partial tomographic luminance data; and means for generating a tomographic image having a striped pattern by combining the partial images.

A processing method according to the present disclosure includes:

a step of, after performing edge detection processing on a tomographic image at each depth, calculating the total number of edge pixels in the tomographic image from 3D tomographic luminance data, and acquiring depth dependence of the number of edges; and a step of extracting a tomographic image having a striped pattern from the depth dependence of the number of edges and the 3D tomographic luminance data.

A non-transitory computer readable medium storing a program according to the present disclosure causes a computer to perform:

calculating, after performing edge detection processing on a tomographic image at each depth, the total number of edge pixels in the tomographic image from 3D tomographic luminance data, and acquiring depth dependence of the number of edges; and extracting a tomographic image having a striped pattern from the depth dependence of the number of edges and the 3D tomographic luminance data.

Advantageous Effects of Invention

According to the present disclosure, it is possible to provide a processing apparatus, a system, and a method capable of extracting an image for accurate authentication, and extracting an image at a high speed.

DESCRIPTION OF EMBODIMENTS

Example embodiments according to the present invention will be described hereinafter with reference to the drawings.

Figure 1:
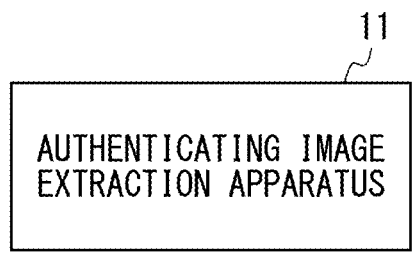
FIG. 1 is a block diagram showing an example of an authentication image extraction apparatus according to an example embodiment.
Figure 2:
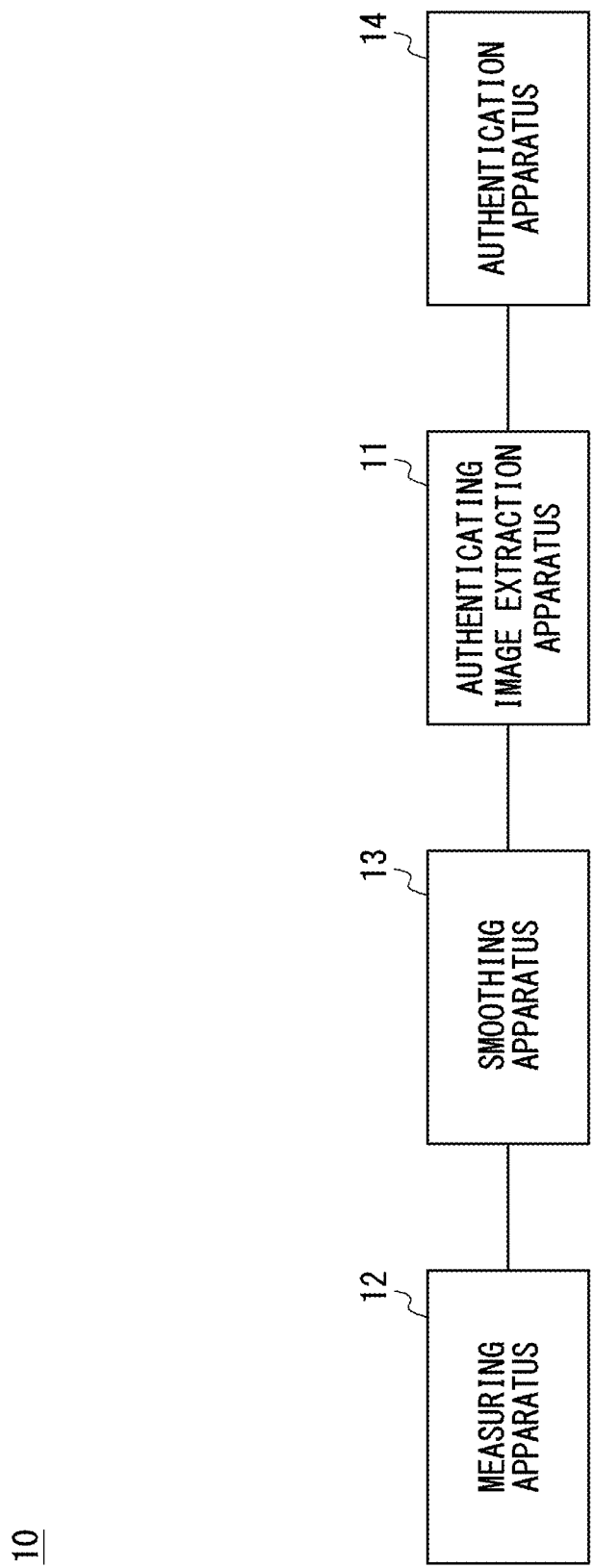
FIG. 2 is a block diagram showing an example of a system according to an example embodiment.

As shown in FIG. 1, an authenticating image extraction apparatus 11 according to an example embodiment is an apparatus for extracting an image or the like used for fingerprint authentication, and details thereof will be described in the descriptions of example embodiments shown below. As shown in FIG. 2, a system 10 according to the example embodiment includes a measuring apparatus 12, a smoothing apparatus 13, the authenticating image extraction apparatus 11, and an authentication apparatus 14.

The measuring apparatus 12 captures 3D (three-dimensional) luminance data such as 3D tomographic luminance data indicating luminance in a 3D space such as in a finger by using the OCT technology or the like. The smoothing apparatus 13 smooths curvatures in a finger or the like in the depth direction thereof in the data acquired by the measuring apparatus 12. Even when the measuring apparatus 12 is an apparatus in which a fingerprint or the like is acquired in a non-contact manner, or by pressing a finger on a glass surface or the like, the roundness of the finger remains. Therefore, the smoothing apparatus 13 smooths curvatures in the depth direction before a process for extracting an authentication image is performed. The authentication apparatus 14 performs biometric authentication by using the extracted image of the fingerprint or the like. Specifically, the authentication apparatus 14 identifies an individual by finding matching between a tomographic image and image data associated with individual information, and comparing the tomographic image with the image data associated with the individual information.

In the following descriptions of example embodiments, a depth from a surface of an epidermis of a finger to the inside of the skin is referred to as a depth or a Z-value, and a plane perpendicular to the depth direction is referred to as an XY-plane. Further, a luminance image on the XY-plane is referred to as a tomographic image.

First Example Embodiment

Figure 3:
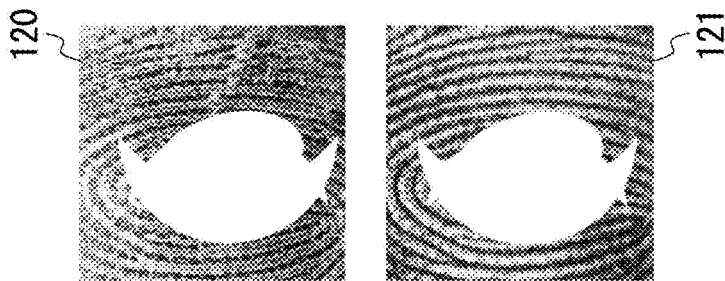
FIG. 3 shows an example of an operation for extracting an authentication image according to first and second example embodiments.
Figure 3:
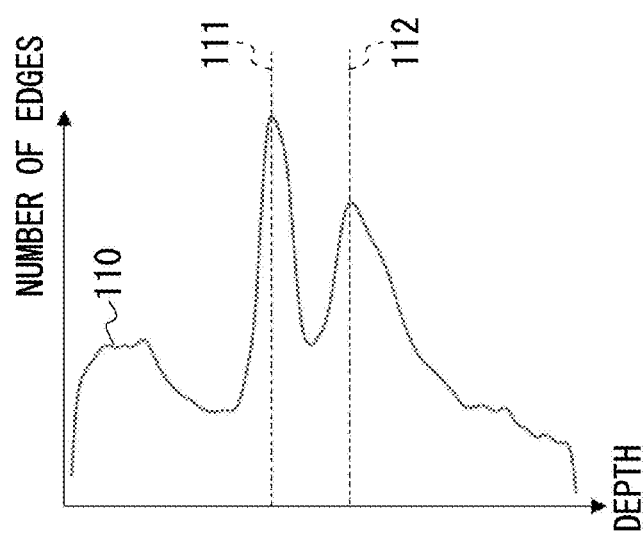
Figure 3:
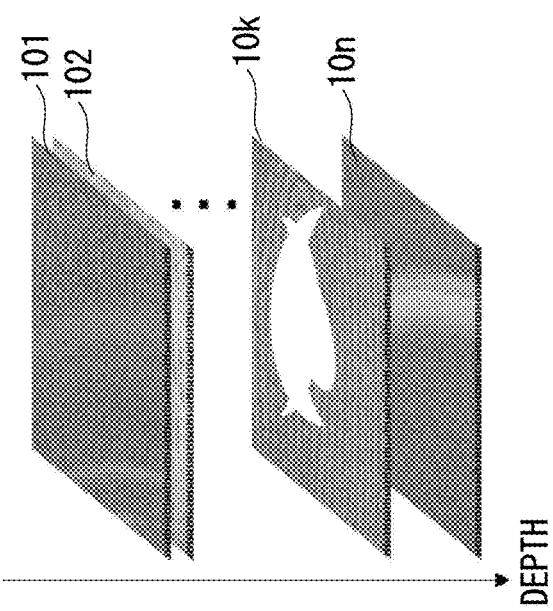

FIG. 3 show images and a graph for explaining an operation of a process for extracting an authentication image according to a first example embodiment of the present invention. Data output from the measuring apparatus 12 through the smoothing apparatus 13 is luminance information at a 3D place, and can be represented by tomographic images 101, 102, ... 10 $k$, ..., and 10$n$ at respective depths as shown in FIG. 3. Note that k is a natural number and n is the total number of tomographic images. A tomographic image at a depth that coincides with the interface between the air and the epidermis shows an epidermal fingerprint most clearly. A tomographic image at a depth that coincides with the interface between the epidermis and the dermis shows a dermal fingerprint most clearly. Therefore, in the present application, attention is paid to the spatial continuity of a fingerprint on the XY-plane when various authentication images are extracted from 3D luminance data, and a depth at which a fingerprint is clearly shown is specified for the use thereof based on the total number of edges in each tomographic image. A graph 110 shows the total numbers of pixels that are determined to be edges in respective tomographic images with respect to the depth direction, which are determined by performing edge detection processing for luminance in the respective tomographic images. As indicted by depths 111 and 112 in the graph, there are two depths at each of which the number of edges has a sharp extreme value. Each of these two depths corresponds to, for example, a depth at which an epidermal fingerprint is clearly shown or a depth at which a dermal fingerprint is clearly shown. In example embodiments described below, an image for authentication is acquired by using the above-described depth dependence of the number of edges.

Figure 4:
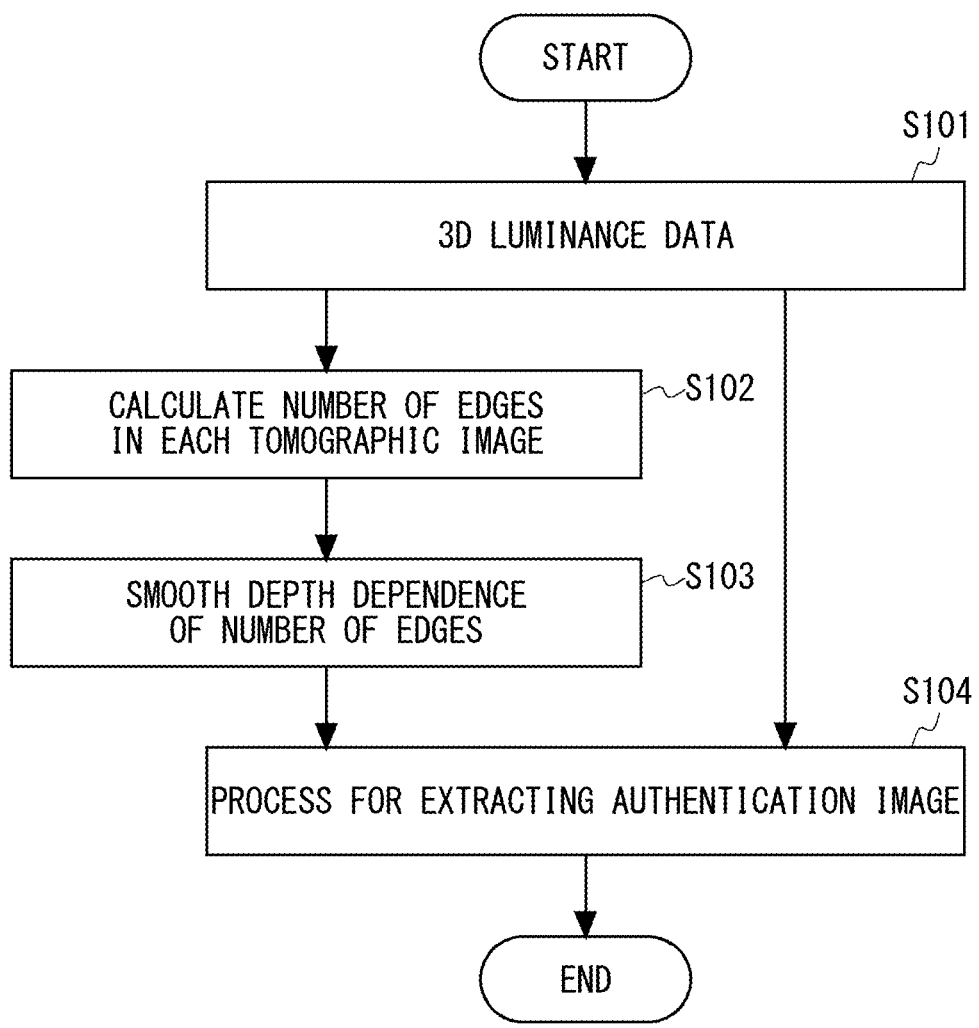
FIG. 4 is a flowchart showing an example of a processing method for extracting a fingerprint image according to the first example embodiment.

FIG. 4 is a flowchart showing an example of a processing method for extracting a fingerprint image according to the first example embodiment of the present invention. The processing method for extracting a fingerprint image according to the first example embodiment can be implemented by using the authenticating image extraction apparatus 11. Firstly, 3D luminance data is acquired (Step S101). Next, a process for determining an edge in a tomographic image at each depth is performed based on the 3D luminance data, and the number of pixels that are determined to be edges is acquired (Step S102). Note that a process for averaging an image at each depth using its neighboring images in order to suppress noises in a tomographic image may be performed before performing the edge determination process in the step S102. Next, a smoothing process is performed for the depth dependence of the number of edges (Step S103). Lastly, a process for extracting a tomographic image having a striped pattern for authentication is performed based on the depth dependence of the number of edges and the 3D luminance data (Authentication Image Extraction Processing Step S104). The tomographic image having a striped pattern is, for example, a fingerprint image.

As described above, the authentication image extraction system according to the first example embodiment can extract an image for authentication from 3D tomographic image data of a finger or the like by using the number of edges in the tomographic image as a feature thereof. As a result, it is possible to extract an image in an adaptive manner against differences of thicknesses of epidermises among individuals. Further, since a depth is determined based on an image having a plurality of pixels, the tolerance to noises is high. Further, since the data to be processed is also the number of depths, the processing can be performed at a high speed as compared to the related art.

Second Example Embodiment

In a second example embodiment, a processing method for extracting an image of an epidermis and an image of a dermal fingerprint in the authentication image extraction processing step S104 in the first example embodiment is described. In FIG. 3, images 120 and 121 show tomographic images at the depths 111 and 112, respectively, at each of which the number of edges has an extreme value, in the graph 110 showing the depth dependence of the number of edges. By acquiring depths having the first and second highest extreme values and selecting corresponding tomographic images at these depths in the graph 110 showing the depth dependence of the number of edges as described above, it is possible to acquire a clear fingerprint image. Further, it is possible to generate and acquire a fingerprint image for authentication by performing additional processes such as conversion into a two-greyscale image and a thinning process.

Figure 5:
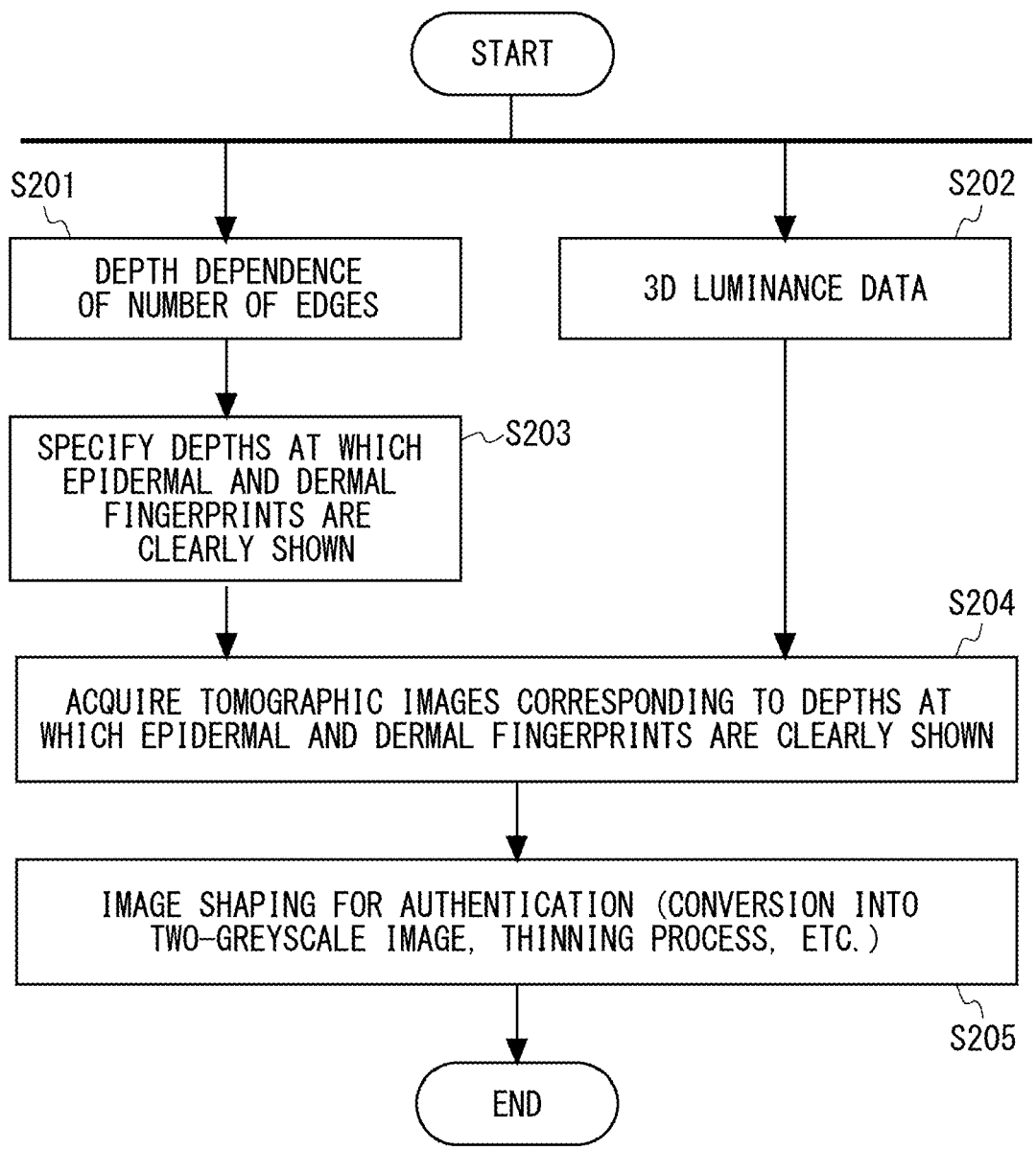
FIG. 5 is a flowchart showing an example of a processing method for extracting a fingerprint image according to the second example embodiment.

FIG. 5 is a flowchart showing an example of a processing method for extracting a fingerprint image according to the second example embodiment of the present invention. In the authentication image extraction processing step S104, depth dependence of the number of edges is acquired (Step S201). Further, 3D luminance data is acquired (Step S202).

After performing the step S201, depths at which an epidermal fingerprint and a dermal fingerprint are clearly shown are specified based on the depth dependence of the number of edges (Step S203). These depths are depths at which the numbers of edges have extreme values and these extreme values are the first and second highest values in the graph 110 showing the depth dependence of the number of edges. One of the two acquired depths that is shallower than the other is determined to be a depth at which an epidermal fingerprint is clearly shown, and the deeper one is determined to be a depth at which a dermal fingerprint is clearly shown.

Next, tomographic images corresponding to the depths at which the epidermal fingerprint and the dermal fingerprint are clearly shown are extracted from the 3D luminance data (Step S204). Note that a process for averaging an image at each depth using its neighboring images in order to suppress noises in the image may be performed when the tomographic images are extracted. The range of depths over which the averaging is preformed may be a specified range, or may be determined based on the shape of protruding parts and the like in the graph of the depth dependence of the number of edges. Lastly, processes for adjusting an image suitable for biometric authentication such as conversion into a two-greyscale image and a thinning process are performed for the fingerprint image extracted in the step S204 (Step S205).

As described above, the authentication image extraction system according to the second example embodiment can extract an image of an epidermal fingerprint and an image of a dermal fingerprint by using information about depths having extreme values in the graph of the depth dependence of the number of edges in the tomographic image. As a result, it is possible to extract a fingerprint image for authentication in an adaptive manner against differences of thicknesses of epidermises among individuals. Further, since a depth is determined based on an image having a plurality of pixels, the tolerance to noises is high. Further, since the data to be processed is also the number of depths, the processing can be performed at a high speed as compared to the related art.

Third Example Embodiment

Figure 6:
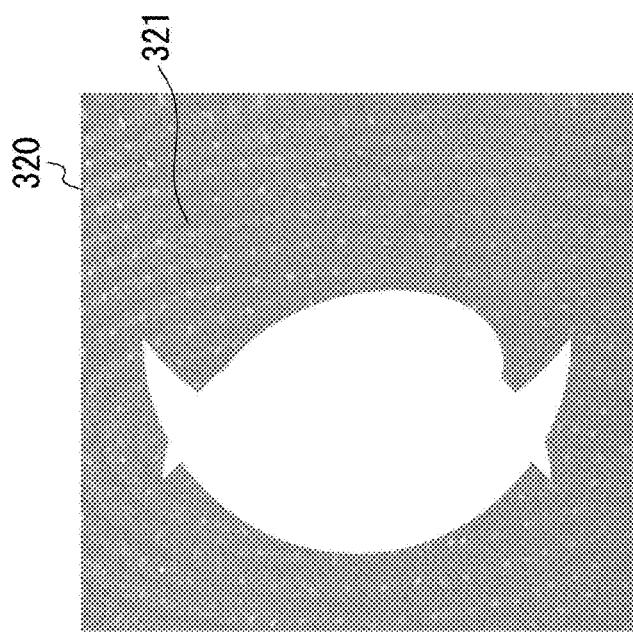
FIG. 6 shows an example of an operation for extracting the position of a sweat gland according to a third example embodiment.
Figure 6:
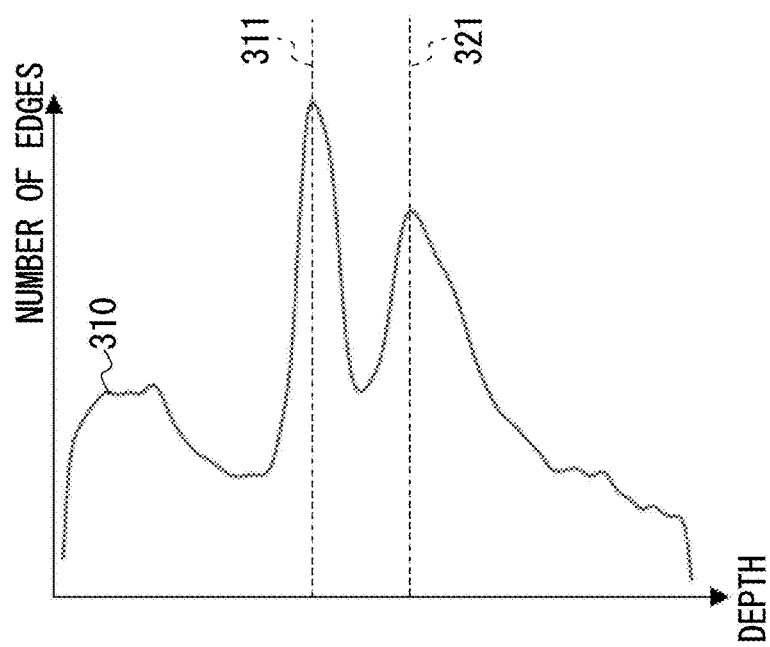

In a third example embodiment, a processing method for extracting an image for specifying the positions of sweat glands in the authentication image extraction processing step S104 in the first example embodiment is described. FIG. 6 is an image and a graph for explaining an operation of a process for extracting an authentication image according to the second example embodiment of the present invention. A graph shown on the left side in FIG. 6 is a graph 310 showing the depth dependence of the number of edges as in the case of the graph shown at the center in FIG. 3. In the graph 310, one of depths having the first and second highest extreme values that is shallower than the other is indicated by a reference numeral 311, and the deeper one is indicated by a reference numeral 312. An image 320 is obtained by averaging tomographic images in the depth direction between the depths 311 and 312. Sweat glands are shown (i.e., appear) as white spots present in the image 320, such as a sweat gland 321. It is possible to perform more accurate authentication by shaping (i.e., converting) the positions of these sweat glands into information that can be used to authenticate a specific image, and providing the obtained information to the authentication apparatus 14.

Figure 7:
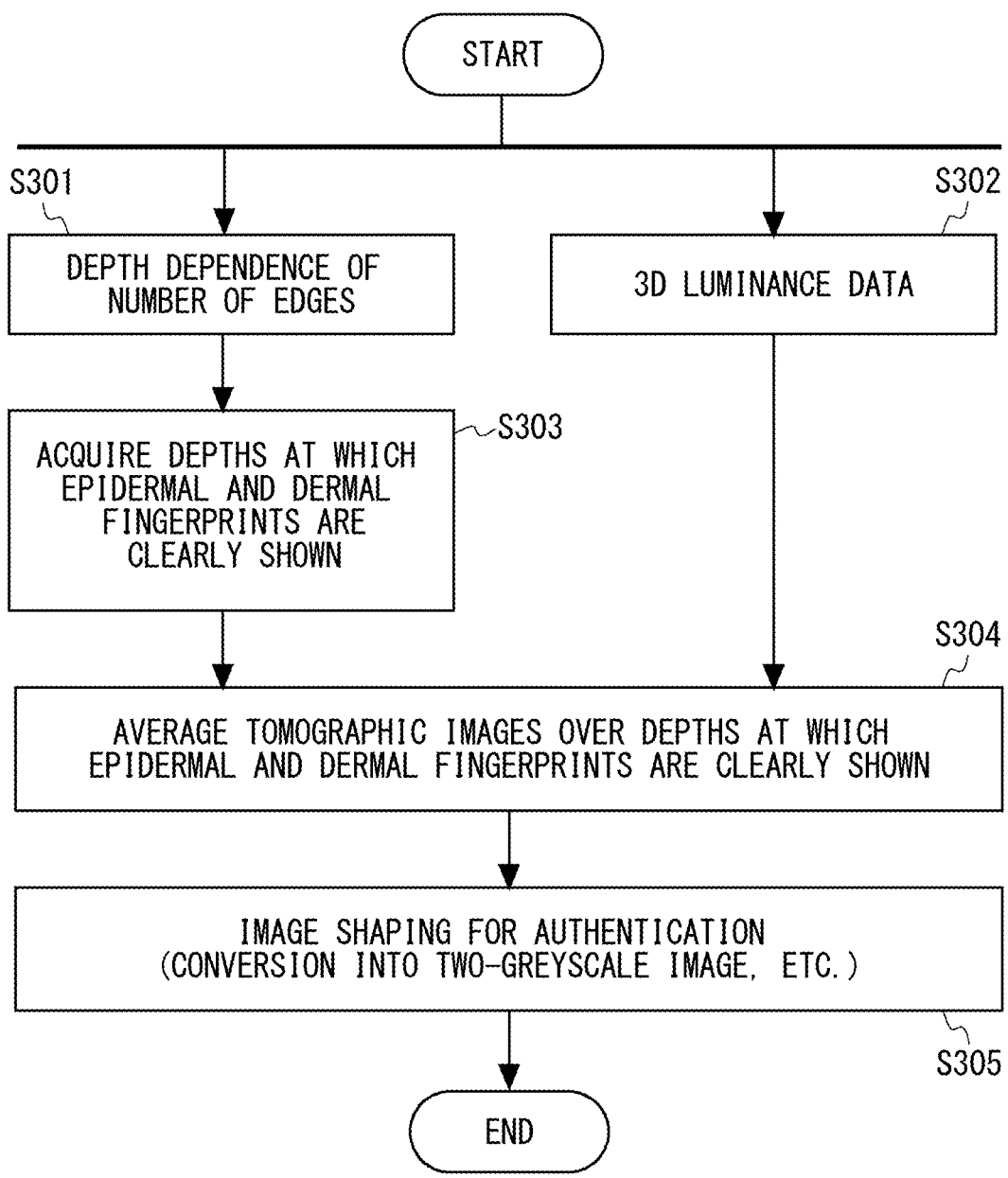
FIG. 7 is a flowchart showing an example of a processing method for extracting an authentication image according to the third example embodiment.

FIG. 7 is a flowchart showing an example of a processing method for extracting an authentication image according to the third example embodiment of the present invention. In the authentication image extraction processing step S104 in the third example embodiment, a depth at which an epidermal fingerprint is clearly shown and a depth at which a dermal fingerprint is clearly shown are extracted as in the case of the second example embodiment. Specifically, firstly, the depth dependence of the number of edges is acquired (Step S301). Further, 3D luminance data is acquired (Step S302). After the step S301 is performed, a depth at which an epidermal fingerprint is clearly shown and a depth at which a dermal fingerprint is clearly shown are specified based on the depth dependence of the number of edges (Step S303).

Next, an authentication image by which the positions of sweat glands can be specified is extracted by performing an averaging process on tomographic images in the depth direction between the depth at which the epidermal fingerprint is clearly shown and the depth at which the dermal fingerprint is clearly shown, both of which have been acquired in the step S303 (Step S304). Note that the depths 311 and 312, between which the averaging process is performed, are indexes, and the averaging process does not necessarily have to be performed over all the tomographic images between the depths 311 and 312. Lastly, image shaping is performed on the image extracted in the step S304, by which the positions of sweat glands can be specified, in order to use the image for authentication (Step S305). Note that the data output in the step S305 may be data in the form of an image or data indicating only the positions of sweat glands on the XY-plane.

As described above, the authentication image extraction system according to the third example embodiment can extract positions at which sweat grands are present by using information about depths having extreme values in regard to the depth dependence of the number of edges in the tomographic image. As a result, it is possible to authenticate not only an ordinary fingerprint image having ridges, branch points, and the like, but also the positions of sweat glands, therefore making it possible to improve the accuracy of authentication and to use it for the determination of a false finger.

Fourth Example Embodiment

In a fourth example embodiment, a process for determining a false finger that is performed before the process for extracting an authentication image in the authentication image extraction processing step S104 in the first example embodiment is described. For example, in the case where a sheet on which a false fingerprint is reprinted is attached onto an actual finger, it is possible to determine a false finger based on the feature of the depth dependence of the number of edges. In such a case, the total number of depths at each of which a fingerprint is clearly shown in the tomographic image is three, i.e., the fingerprint on the sheet, the interface between the air and the epidermis, and the interface between the epidermis and the dermis. Therefore, there are three depths at each of which a sharp extreme value appears in regard to the depth dependence of the number of edges. Next, in the case where the thickness of a sheet on which a false finger is reprinted is large and the interface between the epidermis and the dermis exceeds a measurement range in the depth direction, the number of sharp extreme values in regard to the depth dependence of the number of edges becomes two, but the depth (i.e., the difference) between the extreme values deviates from those of ordinary fingers. Based on these facts, it is possible to determine that a finger could be a false finger when the number of sharp extreme values is three or more, or when the difference between depths having extreme values is equal to or larger than a threshold in the graph of the depth dependence of the number of edges.

Figure 8:
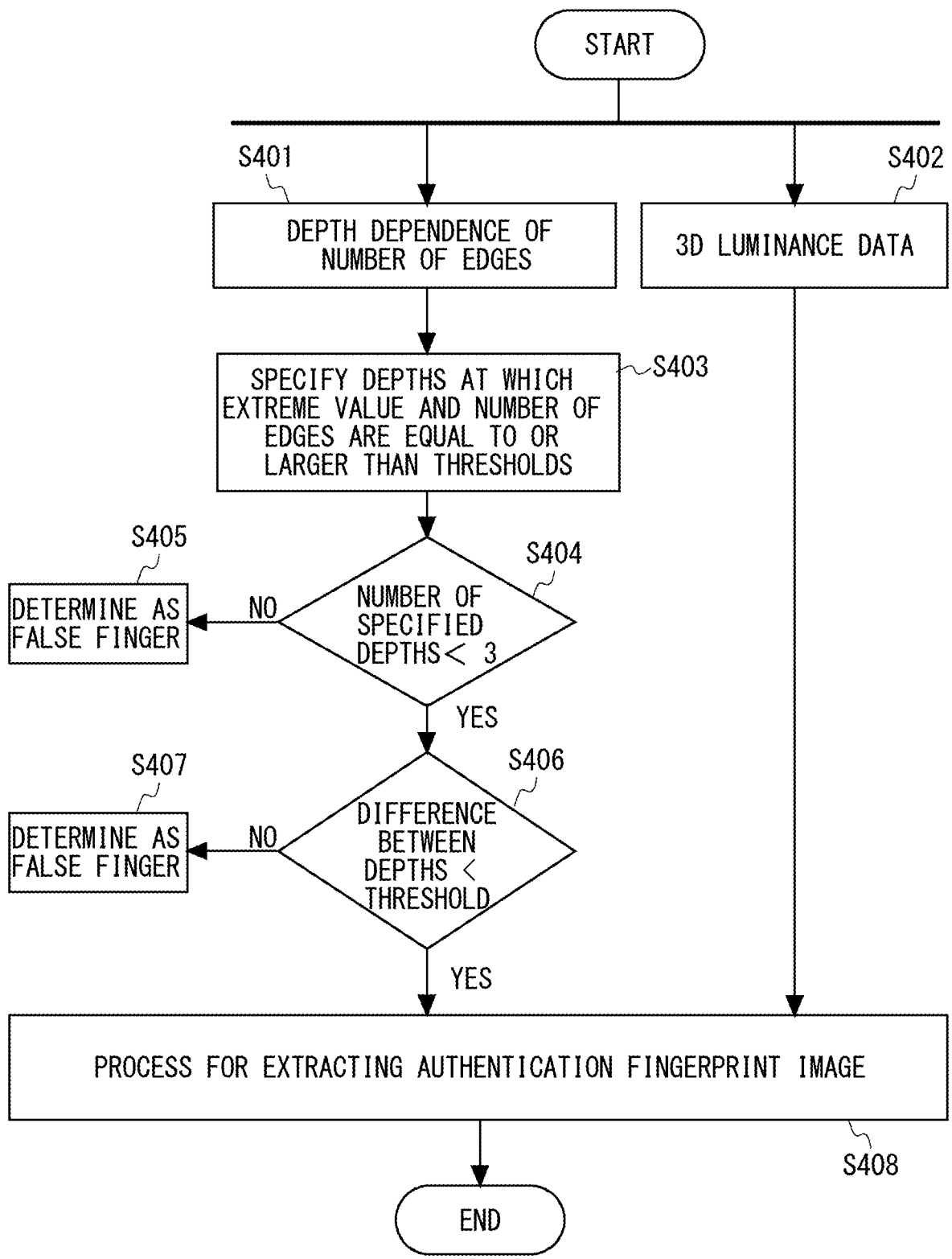
FIG. 8 is a flowchart showing an example of a processing method for extracting an authentication image according to a fourth example embodiment.

FIG. 8 is a flowchart showing an example of a processing method for extracting an authentication image according to the fourth example embodiment of the present invention. In the authentication image extraction processing step S104, depth dependence of the number of edges is acquired (Step S401). Further, 3D luminance data is acquired (Step S402).

After the step S401 is performed, depths each of which has an extreme value and at each of which the number of edges is equal to or greater than a threshold are specified in the graph of the depth-dependence of the number of edges (Step S403). Next, it is determined whether the number of depths specified in the step S403 is less than three or no less than three (Step S404). When the number of depths specified in the step S403 is less than three (Step S404: Yes), it is determined that the finger is an actual finger. On the other hand, when the number of depths specified in the step S403 is equal to or greater than three (Step S404: No), it is determined that the finger is a false finger (Step S405).

Next, it is determined whether the difference between the depth values acquired in the step S403 is smaller than a threshold (Step S406). When the difference between the depths specified in the step S403 is smaller than the threshold (Step S406: Yes), it is determined that the finger is an actual finger. On the other hand, when the difference between the depths specified in the step S403 is equal to or larger than the threshold (Step S404: No), it is determined that the finger is a false finger (Step S407). Lastly, a process for extracting an authentication fingerprint image is performed by the technique described in any of the second and subsequent example embodiments (except for the fourth example embodiment) (Step S408).

As described above, the authentication image extraction system according to the fourth example embodiment can determine whether a finger is an actual finger or a false finger based on information about the depth dependence of the number of edges in the tomographic image.

Fifth Example Embodiment

Figure 9:
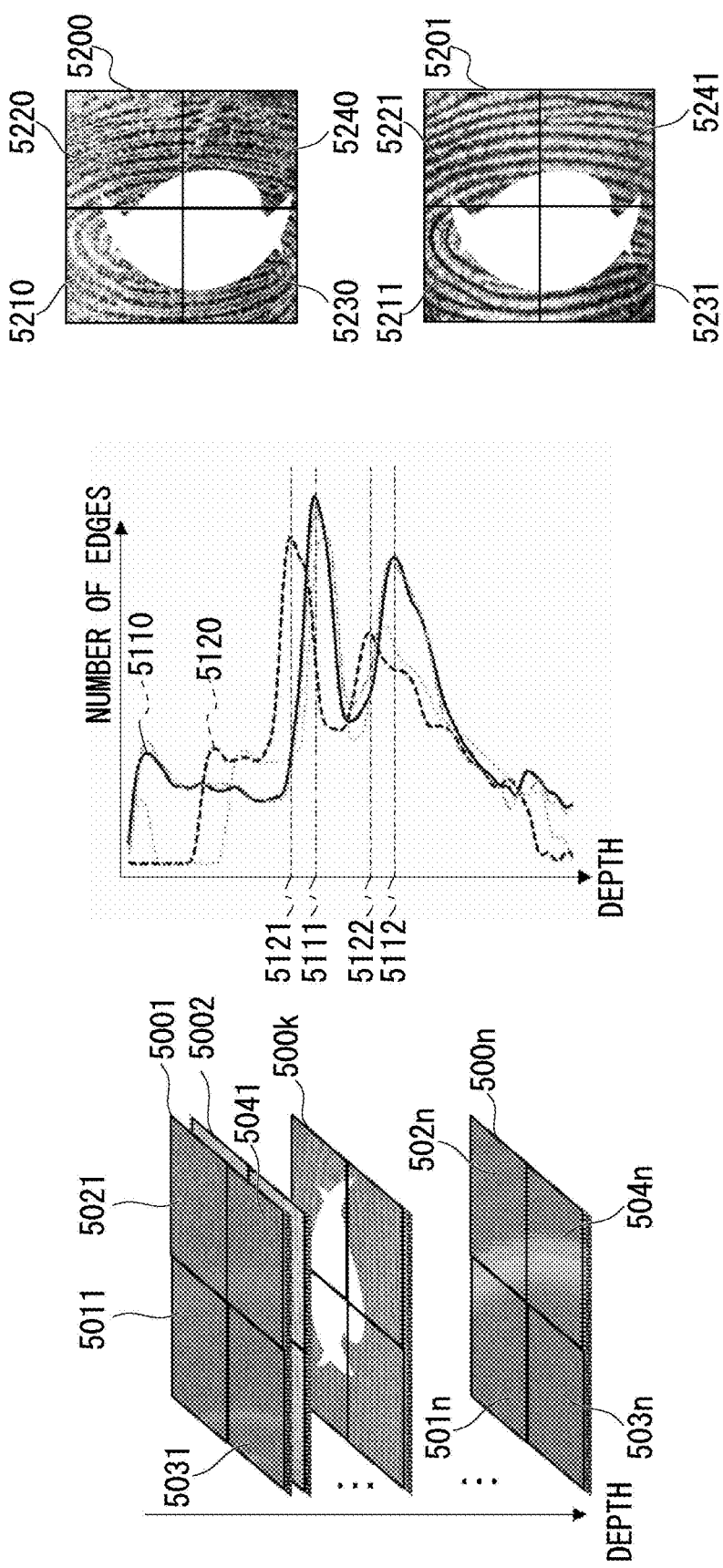
FIG. 9 is a diagram showing an example of an operation for extracting an authentication image by dividing an image according to a fifth example embodiment.

FIG. 9 is a diagram showing an example of an operation of a process for extracting an authentication image according to a fifth example embodiment of the present invention. An image shown on the left side in FIG. 9 shows tomographic images 5001 to 500n at respective depths as in the case of the image shown in FIG. 3. The tomographic image 5001 is divided into four images 5011, 5021, 5031 and 5041 on the XY-planes. Each of the tomographic images 500n at the other depths is also divided into images 501n, 502n, 503n and 504n in a pattern similar to the pattern in the tomographic image 5001. The graphs 5110 and 5120 show examples of the depth dependence of the number of edges for the divided tomographic images 5011 to 501n on the respective XY-planes, and for the divided tomographic images 5021 to 502n on the respective XY-planes, respectively. The depth 5111 is, among the depths corresponding to the tomographic images 5011 to 501n, a depth at which an epidermal fingerprint is shown most clearly. The depth 5112 is, among the depths corresponding to the tomographic images 5011 to 501*n*, a depth at which a dermal fingerprint is shown most clearly. Similarly, the depth 5121 is, among the depths corresponding to the tomographic images 5021 to 502*n*, a depth at which an epidermal fingerprint is shown most clearly. The depth 5122 is, among the depths corresponding to the tomographic images 5021 to 502*n*, a depth at which a dermal fingerprint is shown most clearly. The fingerprint image 5210 is obtained by extracting, among the tomographic images 5011 to 502*n*, a tomographic image at the depth 5111. An epidermal fingerprint image 5200 is acquired by performing the process for each of the sections on the XY-plane, i.e., for the each of the fingerprint images 5220, 5230 and 5240 in a similar manner, and combining the processed sections. A dermal fingerprint image 5201 is acquired by performing a similar procedure, and therefore the description thereof is omitted.

Figure 10:
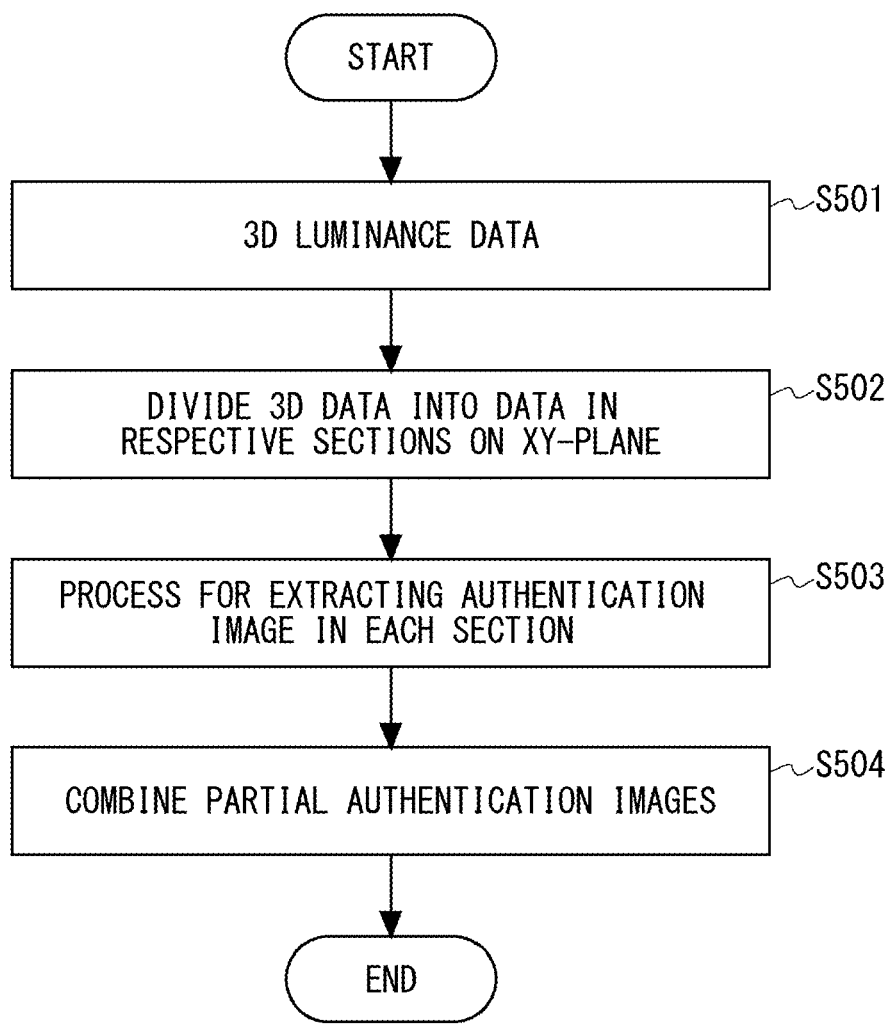
FIG. 10 is a flowchart showing an example of a processing method for extracting an authentication image according to the fifth example embodiment.

FIG. 10 is a flowchart showing an example of a processing method for extracting an authentication image according to the fifth example embodiment of the present invention. It is possible to perform a processing method for extracting an authentication image according to the fifth example embodiment by using the authenticating image extraction apparatus 11. Firstly, 3D luminance data is acquired (Step S501). Next, the 3D luminance data is divided into partial images on the XY-plane (Step S502). In the step S502, the number of sections to which the data is divided is not limited to any number as long as the number of edges can be calculated in each of the divided partial images. Further, the data does not necessarily have to be divided into partial images at equal intervals on the XY-plane. Next, a process for extracting an authentication fingerprint image is performed for each of the partial images (Step S503). The fingerprint image extraction process in the step S503 corresponds to that in any of the example embodiments described in the present disclosure other than the fifth and sixth example embodiments. Lastly, the authentication images extracted from the respective sections of the partial images are combined (Step S504).

Note that the flowchart shown in FIG. 10 is merely an example. For example, after edge pixels in the image are calculated, the image may be divided into partial images, and then a process for extracting an authentication image may be performed for each section.

As described above, the authentication image extraction system according to the fifth example embodiment divides an image into sections on the XY-plane, and can select and extract depths at which fingerprint images are clearly shown in each section. As a result, it is possible acquire a clear fingerprint image even when a fingerprint is distorted in the Z direction due to a blister or the like.

Sixth Example Embodiment

Figure 11:
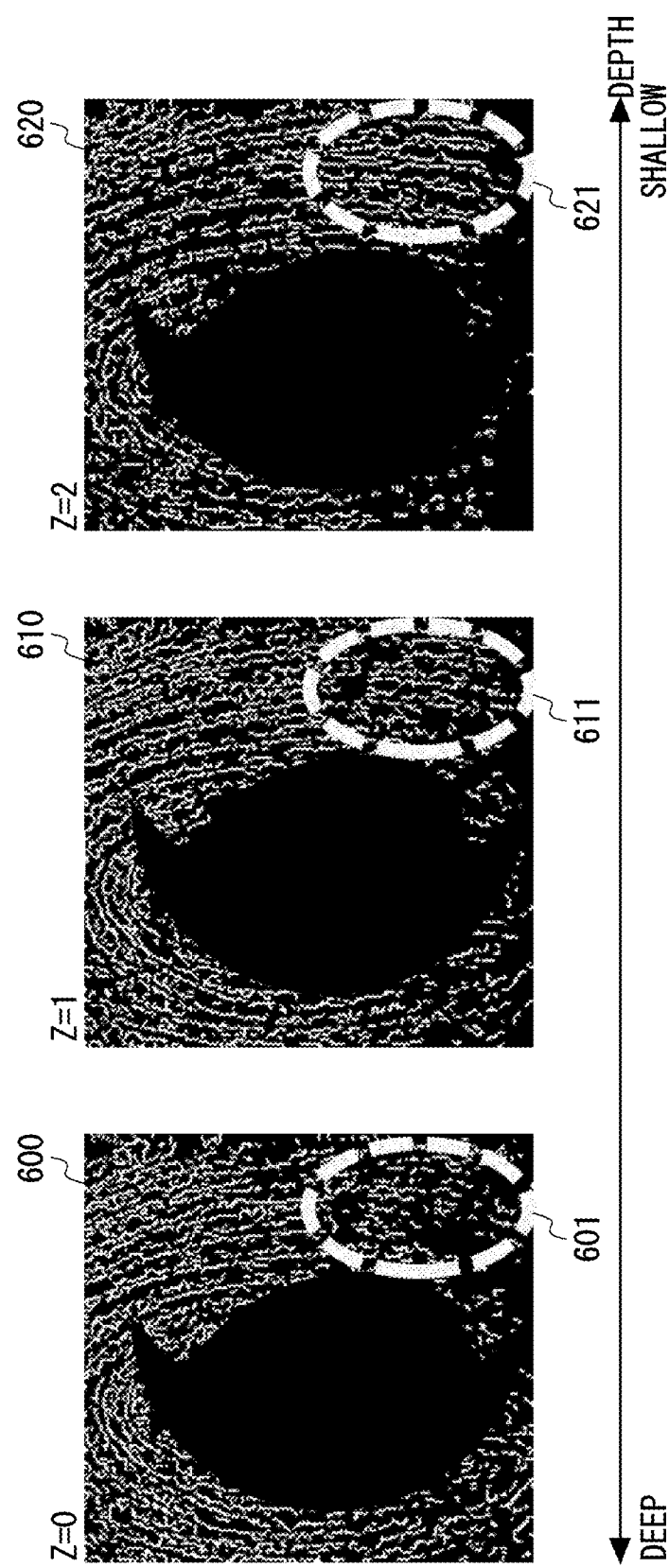
FIG. 11 shows an example of a tracing operation in a depth direction in an edge image according to a sixth example embodiment.

In the description of this example embodiment, an image that is obtained by performing luminance edge detection processing on a tomographic image is referred to as an edge image. FIG. 11 is a drawing for explaining an example of an operation for a process for extracting a fingerprint image according to a sixth example embodiment of the present invention. An image 600 is obtained by performing a process for detecting edges on tomographic images at depths at each of which a fingerprint is clearly shown, specified in the second example embodiment. In a specific area 601 of this edge image, since edges are sparse, the image of the fingerprint is unclear. Images 610 and 620 are edge images at depths shallower than that of the image 600. As shown, edges are dense at other depths as shown in the areas 611 and 621, so that clear fingerprint images can be acquired therefrom. Therefore, it is possible to acquire a clearly fingerprint image by three-dimensionally tracing, from the depth at which a fingerprint in the image 600 is clearly shown, pixels in which edges are present, and combining luminance information at the depths in which edges are present.

Figure 12:
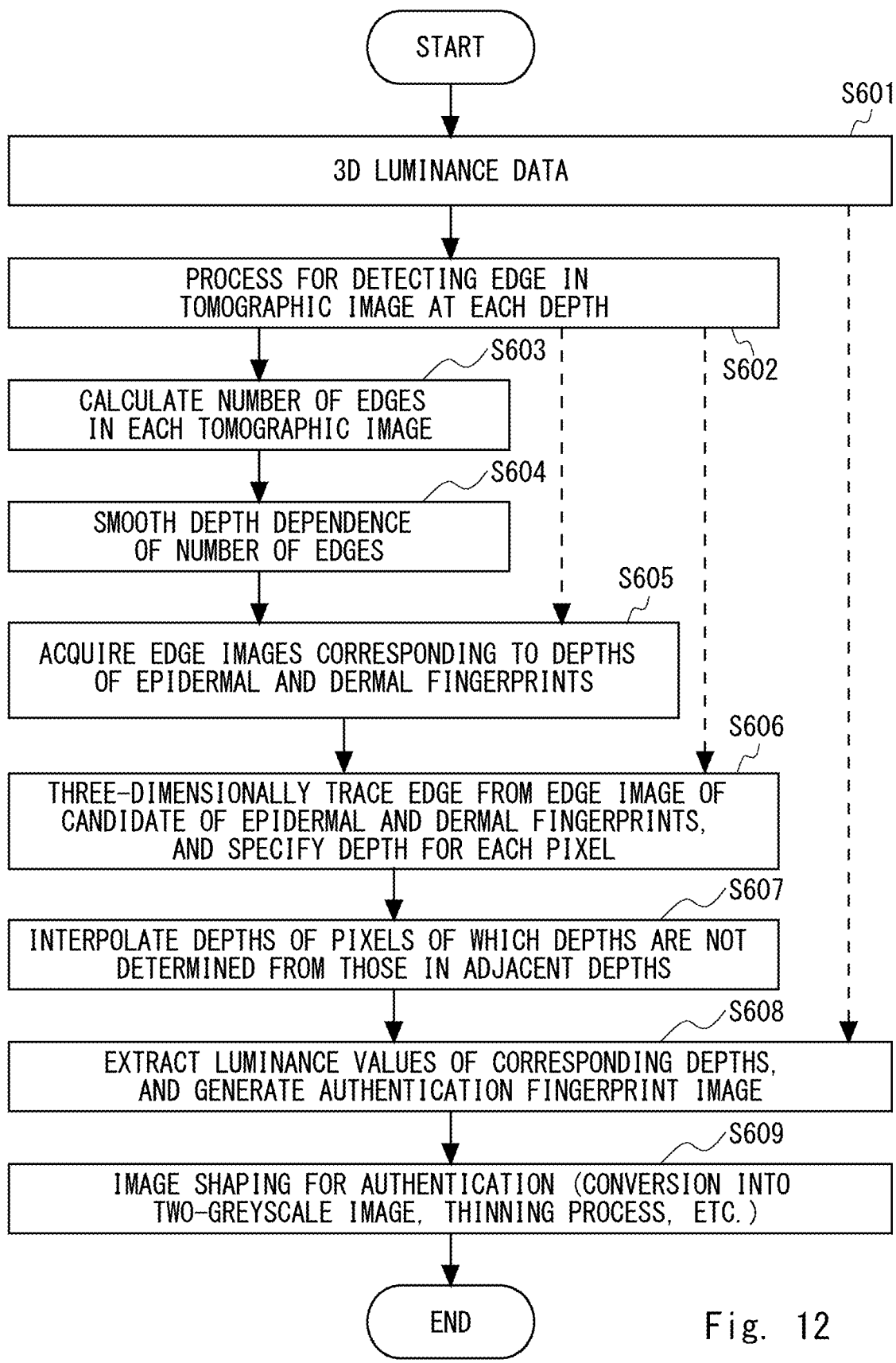
FIG. 12 is a flowchart showing an example of a processing method for extracting a fingerprint image according to the sixth example embodiment.

FIG. 12 is a flowchart showing an example of a processing method for extracting a fingerprint image according to the sixth example embodiment of the present invention. Note that solid-line arrows in FIG. 12 indicate a flow of the processing method. Doted-line arrows in FIG. 12 indicate flows of data such as images in a supplemental manner, and do not indicate the flow of the processing method. It is possible to perform a processing method for extracting an authentication image according to the sixth example embodiment by using the authenticating image extraction apparatus 11. Firstly, 3D luminance data is acquired (Step S601). Next, for a tomographic image at each depth, an edge image is acquired based on the 3D luminance data (Step S602). Next, similarly to the step S102, for a tomographic image at each depth, edge pixels present in that tomographic image are counted (Step S603). Next, similarly to the step S103, the depth dependence of the number of edges is smoothed (Step S604). Next, depths at which an epidermal fingerprint and a dermal fingerprint are clearly shown are specified based on the depth dependence of the number of edges. Then, for each of the specified depths, an edge image corresponding to that depth is acquired (Step S605). Next, depths at which edges images are present are determined for the XY-plane by three-dimensionally tracing, from the edge images at the depths at which the epidermal fingerprint and the dermal fingerprint are clearly shown, pixels in which edges are present (Step S606). When edges are present at a plurality of depths in the step S606, a value close to the depth specified in the step S605 is used. Next, for pixels of which the depths at which edges are present on the XY-plane are not determined, depth values are interpolated and assigned based on those of adjacent pixels (Step S607). Next, an authentication fingerprint image is generated by extracting, for each pixel, a luminance value corresponding to the depth value of that pixel from the 3D luminance data (Step S608). Next, similarly to other example embodiments, in the extraction of luminance values in the step S608, noises may be suppressed by averaging the luminance value at the target depth by using those at its neighboring depths. Lastly, the authenticating image extraction apparatus 11 performs processes for adjusting an image for authentication, such as conversion into a two-greyscale image and a thinning process, on the extracted fingerprint image (Step S609).

As described above, the authentication image extraction system according to the fifth example embodiment can select and extract depths at each of which a fingerprint image is clearly shown by three-dimensionally searching edge images. As a result, it is possible acquire a clear fingerprint image even when a fingerprint is distorted in the Z direction due to a blister or the like.

Other Example Embodiments

Note that although the present invention is described as a hardware configuration in the above-described first to sixth example embodiments, the present invention is not limited to the hardware configurations. In the present invention, the processes in each of the components can also be implemented by having a CPU (Central Processing Unit) execute a computer program.

Figure 13:
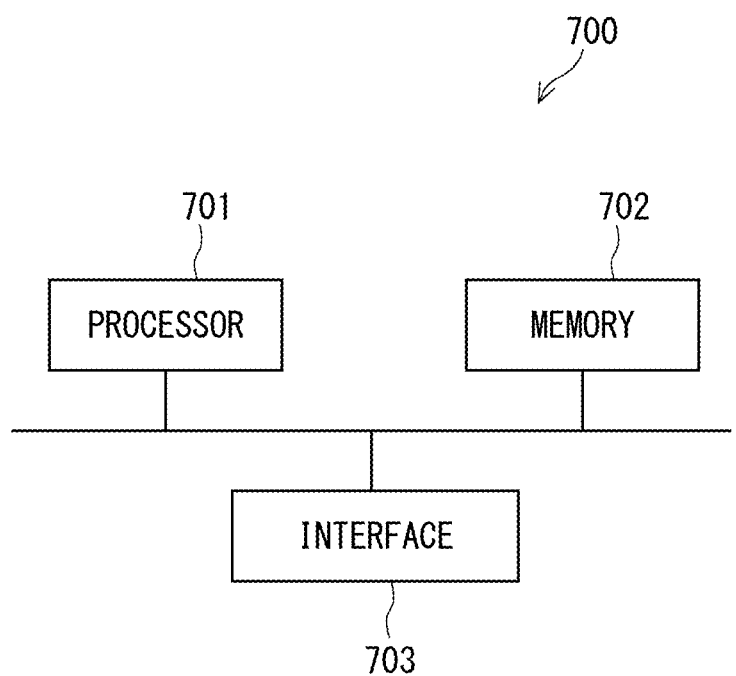
FIG. 13 shows an example of a hardware configuration included in an authentication image extraction apparatus.

For example, the authenticating image extraction apparatus 11 according to any of the above-described example embodiments can have the below-shown hardware configuration. FIG. 13 shows an example of a hardware configuration included in the authenticating image extraction apparatus 11.

An apparatus 700 shown in FIG. 13 includes a processor 701 and a memory 702 as well as an interface 703. The authenticating image extraction apparatus 11 described in any of the above example embodiments is implemented as the processor 701 loads and executes a program stored in the memory 702. That is, this program is a program for causing the processor 701 to function as the authenticating image extraction apparatus 11 shown in FIG. 1 or a part thereof. This program can be considered to be a program for causing the authenticating image extraction apparatus 11 of FIG. 1 to perform the processing in the authenticating image extraction apparatus 11 or a part thereof.

The above-described program may be stored by using various types of non-transitory computer readable media and supplied to a computer (computers including information notification apparatuses). Non-transitory computer readable media include various types of tangible storage media. Examples of the non-transitory computer readable media include magnetic recording media (e.g., a flexible disk, a magnetic tape, and a hard disk drive), and magneto-optical recording media (e.g., a magneto-optical disk). Further, the example includes a CD-ROM (Read Only Memory), a CD-R, and a CD-R/W. Further, the example includes a semiconductor memory (e.g., a mask ROM, a PROM, an EPROM, a flash ROM, and a RAM). Further, the program may be supplied to a computer by various types of transitory computer readable media). Examples of the transitory computer readable media include an electrical signal, an optical signal, and electromagnetic waves. Transitory computer readable media can provide the program to a computer via a wired communication line (e.g., electric wires, and optical fibers) or a wireless communication line.

Further, as described above as the procedure for processing in the authenticating image extraction apparatus 11 in the above-described various example embodiments, the present invention may also be applied as a processing method.

REFERENCE SIGNS LIST

10 SYSTEMS
11 AUTHENTICATION IMAGE EXTRACTION APPARATUS
12 MEASURING APPARATUS
13 SMOOTHING APPARATUS
14 AUTHENTICATION APPARATUS
101, 102, 10k, 10n, 5001, 5002, 500k, 500n TOMOGRAPHIC IMAGE
110, 310, 5110, 5120 GRAPH (DEPTH DEPENDENCE OF NUMBER OF EDGES)
111, 311, 5111, 5121 DEPTH (DEPTH AT WHICH EPIDERMAL FINGERPRINT IS EXTRACTED)
112, 312, 5112, 5122 DEPTH (DEPTH AT WHICH DERMAL FINGERPRINT IS EXTRACTED)
120, 5200 IMAGE (EPIDERMAL FINGERPRINT IMAGE)
121, 5201 IMAGE (DERMAL FINGERPRINT IMAGE)
320 IMAGE (SWEAT GLAND IMAGE)
321 SWEAT GLAND
5011, 5021, 5031, 5041, 501n, 502n, 503n, 504n IMAGE (DIVIDED TOMOGRAPHIC IMAGE OF EPIDERMAL FINGERPRINT)
5210, 5220, 5230, 5240 FINGERPRINT IMAGE (DIVIDED TOMOGRAPHIC IMAGE OF EPIDERMAL FINGERPRINT)
5211, 5221, 5231, 5241 DIVIDED TOMOGRAPHIC IMAGE OF DERMAL FINGERPRINT
600, 610, 620 IMAGE (EDGE IMAGE)
601, 602, 603 SPECIFIC AREA OF EDGE IMAGE
700 APPARATUS
701 PROCESSOR
702 MEMORY
703 INTERFACES

What is claimed is:

1. A processing apparatus comprising:
one or more processors;
a memory storing executable instructions that, when executed by the one or more processors, causes the one or more processors to perform as:
a unit that, after performing edge detection processing on a tomographic image at each depth, calculates the total number of edge pixels in the tomographic image from 3D (three-dimensional) tomographic luminance data, and acquires depth dependence of the number of edges; and
a unit that extracts a tomographic image having a striped pattern from the depth dependence of the number of edges and the 3D tomographic luminance data.

2. The processing apparatus according to claim 1, wherein a biological feature image containing a feature of a living body is extracted from 3D tomographic luminance data of the living body.

3. The processing apparatus according to claim 2, wherein an extraction unit that extracts the biological feature image comprises:
a calculation unit that obtains depth values at which extreme values in the depth dependence of the number of edges become first and second highest values; and
a unit that extracts an image containing information about an epidermis and a dermis from the 3D tomographic luminance data based on the depth values.

4. The processing apparatus according to claim 2, wherein a unit that extracts the biological feature image comprises:
a calculation unit that obtains depth values at which extreme values in the depth dependence of the number of edges become first and second highest values; and
a unit that specifies a position of a sweat gland from the 3D tomographic luminance data based on a tomographic luminance image between the depth values.

5. The processing apparatus according to claim 2, wherein a unit that extracts the biological feature image comprises:
a unit that calculates the number of extreme values exceeding a threshold and a difference between depths having the extreme values in the depth dependence of the number of edges; and
a unit that determines that biometric information is false when the number of extreme values is larger than three or when the difference between the depths exceeds a threshold.

6. A fingerprint image extraction processing apparatus comprising:
a dividing unit that acquires 3D partial luminance data by dividing the 3D tomographic luminance data at a plane perpendicular to a direction toward inside of a target object;
a unit that extracts a partial image having a striped pattern from the 3D partial luminance data by using a processing apparatus according to claim 1; and a unit that generates a tomographic image having a striped pattern by combining the partial images.

7. The processing apparatus according to claim 1, further comprising:
a unit that detects an edge in a tomographic image at each depth in the 3D tomographic luminance data and calculates 3D edge data;
a calculation unit that acquires depth values at which extreme values in the depth dependence of the number of edges become first and second highest values;
a unit that traces an edge in 3D directions from a tomographic edge image corresponding to the depth value based on the 3D edge data and extracts a depth at which an edge is present in each pixel; and
a unit that extracts a tomographic image having a striped pattern based on the depth at which the edge is present.

8. A system comprising:
an apparatus configured to acquire 3D tomographic luminance data of a target object; and
a processing apparatus according to claim 1, wherein
the system is configured to acquire a tomographic image having a striped pattern inside the target object.

9. A biometric authentication system comprising:
an apparatus configured to acquire 3D tomographic luminance data of a living body;
a processing apparatus according to claim 1; and
a processing apparatus configured to compare a tomographic image having a striped pattern with image data associated with individual information, wherein
the system is configured to identify an individual by a comparison between the tomographic image and the image data.

10. A processing method comprising:
a step of, after performing edge detection processing on a tomographic image at each depth, calculating the total number of edge pixels in the tomographic image from 3D tomographic luminance data, and acquiring depth dependence of the number of edges; and
a step of extracting a tomographic image having a striped pattern from the depth dependence of the number of edges and the 3D tomographic luminance data.

11. A non-transitory computer readable medium storing a program for causing a computer to perform:
calculating, after performing edge detection processing on a tomographic image at each depth, the total number of edge pixels in the tomographic image from 3D tomographic luminance data, and acquiring depth dependence of the number of edges; and
extracting a tomographic image having a striped pattern from the depth dependence of the number of edges and the 3D tomographic luminance data.

* * * * *